(12) United States Patent
Marraccini et al.

(10) Patent No.: US 6,617,433 B1
(45) Date of Patent: Sep. 9, 2003

(54) COFFEE STORAGE PROTEINS

(75) Inventors: Pierre Marraccini, Savonnieres (FR); John Rogers, Saint-Cyr-sur-Loire (FR)

(73) Assignee: Nestec S.A., Vevey (CH)

( * ) Notice: Subject to any disclaimer, the term of this patent is extended or adjusted under 35 U.S.C. 154(b) by 0 days.

(21) Appl. No.: 09/462,720

(22) PCT Filed: Jun. 25, 1998

(86) PCT No.: PCT/EP98/04038

§ 371 (c)(1),
(2), (4) Date: Apr. 11, 2000

(87) PCT Pub. No.: WO99/02688

PCT Pub. Date: Jan. 21, 1999

(30) Foreign Application Priority Data

Jul. 12, 1997 (EP) .............................................. 97202183

(51) Int. Cl.[7] ........................ A61K 35/78; C07K 14/00; A01H 5/00

(52) U.S. Cl. ........................ 530/370; 530/378; 530/350; 800/298

(58) Field of Search ................................ 530/370, 378, 530/350; 800/298

(56) References Cited

PUBLICATIONS

Acuna et al. "11s storage globulin from Coffea arabica seeds", May 1, 1997, Accession No.: P93079, Database: SPTREMBL_16.*

* cited by examiner

*Primary Examiner*—Christopher S. F. Low
*Assistant Examiner*—Rita Mitra
(74) *Attorney, Agent, or Firm*—Winston & Strawn

(57) ABSTRACT

The present invention relates to proteins derived from the coffee bean and DNAs encoding and regulating the expression of at least one of these proteins.

4 Claims, 1 Drawing Sheet

COFFEE STORAGE PROTEINS

This application was filed as a 35 U.S.C. 371 application of PCT International Application NO. PCT/EP98/04038 on Jun. 25, 1998, which claims priority to a foreign application EP 97202183.6 filed on Jul. 12, 1997.

TECHNICAL FIELD

The subject of the present invention is proteins derived from the coffee bean, and DNAs encoding and regulating the expression of at least one of these proteins.

BACKGROUND

It is known that numerous plants are capable of producing, in their embryos, in their tubers and in particular in their seeds, storage proteins during their growth. These storage proteins play an important role, in particular, in the storage of amino acids for germination of the seed. They are also important in the structure and the content of amino acids.

Some of these proteins have been isolated and, in some cases, have been expressed in host plants.

Thus, EP 0,295,959 demonstrates, in particular, the expression, in a host plant, of the DNA derived from *Bertholletia excelsa* H.B.K. (brazil nut) encoding at least one subunit of the storage protein called 2S.

Furthermore, WO 9119801 demonstrates the existence of two storage proteins derived from *Theobroma cacao*, their precursor and their genes encoding these proteins.

However, up until now, no storage protein derived from the coffee bean and no sequence capable of regulating the transcription of these proteins are known. Yet, it would be very useful to have available sequences of such proteins, in particular in order to modify the original production of the storage proteins in the coffee bean. Furthermore, it would also be very useful to have available a sequence capable of regulating the transcription of such proteins, so as to allow, in particular, the expression, in the coffee bean, of a protein encoded by a gene of interest.

The aim of the present invention is to respond to these needs.

SUMMARY OF THE INVENTION

To this effect, the present invention relates to any DNA derived from the coffee bean, encoding at least 20 consecutive amino acids of the amino acid sequence SEQ ID NO:2.

The present invention relates to any storage protein derived from the coffee bean, having at least 20 consecutive amino acids of the amino acid sequence SEQ ID NO:2.

Another subject of the present invention relates to all or part of the DNA delimited by nucleotides 1 to 2509 of the nucleic sequence SEQ ID NO:3, capable of regulating the transcription of the storage proteins according to the invention, as well as the use of all or part of this DNA to direct the expression of genes of interest in plants, in particular in the coffee tree.

The present invention also relates to the use of all or part of the DNA delimited by nucleotides 33 to 1508 of the nucleic sequence SEQ ID NO: 1 or of its complementary strand, of at least 10 bp, to carry out a PCR or as probe to detect in vitro or to inactivate in vivo a coffee bean gene encoding a storage protein.

Furthermore, the invention relates to any recombinant plant cell capable of expressing a recombinant storage protein according to the invention.

Finally, the present invention relates to any food, cosmetic or pharmaceutical product comprising all or part of the DNA or of the recombinant proteins according to the invention.

The present invention therefore opens the possibility of using all or part of the DNA according to the invention so as to modify the original production of the storage proteins in the coffee bean. It is therefore possible in particular to envisage overexpressing or underexpressing the expression of all or part of the DNA according to the invention in the coffee bean.

DETAILED DESCRIPTION OF THE INVENTION

Figure 1:
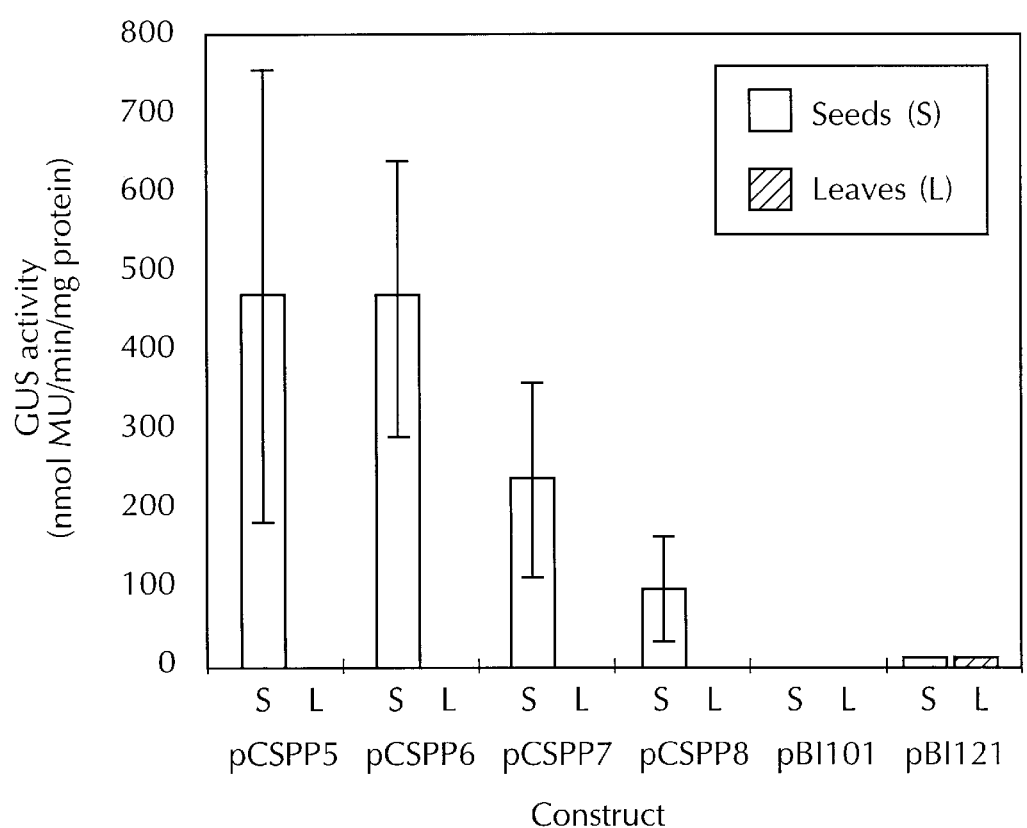
FIG. 1 is a graphical representation of GUS activity in leaves and seeds of transgenic tobacco plants.

For the purposes of the present invention, "homologous nucleic sequence" is understood to mean any nucleic sequence differing from the nucleic sequences according to the invention only in the substitution, deletion and/or insertion of a small number of base pairs. In this context, two nucleic sequences which, because of the degeneracy of the genetic code, encode the same protein will be considered in particular as being homologous. Will also be considered as homologous sequence, that which exhibits more than 70% homology with the nucleic sequence according to the invention. In the latter case, the homology is determined by the ratio between the number of base pairs of a homologous sequence and that of a nucleic sequence according to the invention.

Furthermore, for the purposes of the present invention, homologous nucleic sequence is also understood to mean a sequence which hybridizes under stringent conditions, that is to say any nucleic sequence capable of hybridizing to the nucleic sequences according to the present invention by the Southern-Blot method, so as to avoid a specific hybridizations or hybridizations which are not very stable (Sambrook et al. Molecular Cloning, A Laboratory Manual, Cold Spring Harbor Laboratory Press, USA, 1989, chapter 9.31 to 9.51).

Finally, for the purposes of the present invention, "homologous amino acid sequence" is understood to mean any amino acid sequence differing from the amino acid sequences according to the present invention only in the substitution, insertion and/or deletion of at least one amino acid. Will also be considered as homologous sequence, that which exhibits more than 50% homology with the amino acid sequence according to the invention. In the latter case, the homology is determined by the ratio between the number of amino acids of a homologous sequence and that of an amino acid sequence according to the invention.

In the remainder of the description, the sequences SEQ ID NO: refer to the sequences presented in the sequence listing hereinafter. The synthetic oligonucleotides SEQ ID NO: 5 to SEQ ID NO: 18, which are mentioned in the description and presented in the sequence listing hereinafter, are provided by Genset SA, 1 passage Delaunay, 75011 Paris, France.

Storage proteins are present only in the coffee bean and are highly expressed in the endosperm. In the ripe coffee bean, they represent nearly 50% of the total proteins and play a major role in the maturation of the coffee bean. These proteins influence in particular the structure and the density of the coffee bean as well as its amino acid content. They also play a major role in the storage of amino acids for the germination of the bean.

It is possible to isolate the DNA encoding, as well as the DNA regulating the expression of the storage proteins of the coffee bean by carrying out a conventional inverse PCR starting with nucleic primers derived from the nucleic sequences SEQ ID NO: 1 and SEQ ID NO: 3. Persons skilled in the art are indeed capable of choosing the primers which are most suitable for carrying out this PCR, for example.

To this effect, a DNA encoding at least 20 consecutive amino acids of the amino acid sequence SEQ ID NO: 2 has been isolated from the coffee bean.

Preferably, said DNA encodes at least one protein derived from the coffee bean, chosen from the group comprising the storage protein αβ, having the amino acid sequence SEQ ID NO: 2, the cleavage protein α delimited in the amino acid sequence SEQ ID NO: 2 by amino acids 1 to 304, the cleavage protein β, delimited in the amino acid sequence SEQ ID NO: 2 by amino acids 305 to 492, or any nucleic sequences homologous to these sequences.

Given the benefit of the present invention, the invention relates to the DNA delimited by nucleotides 33 to 1508 in the nucleic sequence SEQ ID NO: 1 encoding the storage protein αβ, or any nucleic sequence, homologous to this sequence. In particular, the invention relates to the DNA comprising at least in the nucleic sequence SEQ ID NO: 1 nucleotides 33 to 944 encoding the cleavage protein α and/or nucleotides 945 to 1508 encoding the cleavage protein β.

The present invention also relates to the use of all or part of the DNA delimited by nucleotides 33 to 1508 of the nucleic sequence SEQ ID NO: 1 or of its complementary strand, of at least 10 bp as primer to carry out a PCR or as probe to detect in vitro or to modify the expression in vivo of at least one coffee bean gene encoding at least one storage protein.

The DNA according to the present invention may be advantageously used to express at least one recombinant storage protein, derived from the coffee bean, in a host plant or microorganism. To this effect, it is possible to clone all or part of the nucleic sequence SEQ ID NO: 1 delimited by nucleotides 33 to 1508 into an expression vector downstream of a promoter, or of a promoter and a signal sequence, and upstream of a terminator, while preserving the reading frame, then the said vector may be introduced into a plant, a yeast or bacterium, for example. Specific examples of application are presented hereinafter.

Furthermore, all or part of the DNA delimited by nucleotides 33 to 1508 of nucleic sequence SEQ ID NO: 1 may be advantageously used in the coffee bean in a form which is modified by mutagenesis so as to modify the original production of storage proteins in the coffee bean and thus to modify the organoleptic quality of the coffee bean.

The invention also relates to the storage protein αβ, having the amino acid sequence SEQ ID NO: 2, the cleavage protein α having the sequence delimited by amino acids 1 to 304 of the amino acid sequence SEQ ID NO: 2 and the cleavage protein β having the sequence delimited by amino acids 305 to 492 of the amino acid sequence SEQ ID NO: 2, or any amino acid sequence which is homologous thereto.

The fact that the storage proteins derived from the coffee bean are synthesized into a large precursor, the storage protein αβ, which is cleaved into two proteins, the cleavage protein α and the cleavage protein β, has been demonstrated. The cleavage proteins α and β can recombine in a polymerized form through at least one disulphide bridge. Indeed, it has been possible to isolate in the endosperm of the coffee bean polymerized forms of the cleavage proteins α and/or β and/or of their homologous sequences.

To this effect, the present invention also relates to the polymerized form of the recombinant storage proteins αβ, α and/or β, as well as their homologous sequences.

Another subject of the present invention relates to all or part of the DNA delimited by nucleotides 1 to 2509 of the nucleic sequence SEQ ID NO: 3, capable of regulating the expression of the storage protein having the amino acid sequence SEQ ID NO: 2.

The invention also relates to the use of all or part of the DNA delimited by nucleotides 1 to 2509 of the nucleic sequence SEQ. ID NO: 3, to allow the expression, in the coffee bean or in a heterologous plant, of the storage protein αβ encoded by nucleotides 33 to 1508 of the nucleic sequence SEQ ID NO: 1 or of a protein encoded by a gene of interest.

The DNA delimited by nucleotides 1 to 2509 of the nucleic sequence SEQ ID NO: 3 may be advantageously used by fusing it, completely or partially, with a gene of interest, while preserving the reading frame, and then by cloning the whole into an expression vector which is introduced into coffee, so as to allow the expression of the protein encoded by this gene in the coffee bean.

The invention also covers all the food, cosmetic or pharmaceutical products comprising all or part of the DNA, or of the recombinant proteins according to the invention. Persons skilled in the art are indeed capable, by means of oligonucleotide probes or of appropriate antibodies, of detecting their presence in very low quantities.

The storage proteins derived from the coffee bean, the DNA derived from the coffee bean encoding at least one of these proteins, as well as the DNA capable of regulating their transcription, according to the present invention, are characterized in greater detail with the aid of biochemical and molecular analyses hereinafter.

I. Identification of the Storage Proteins of the Coffee Bean

The total proteins are extracted from ripe fruits of *Coffea arabica* of the Caturra variety.

To do this, the maternal tissues are separated from the coffee beans which are rapidly ground in liquid nitrogen, and which are then reduced to a powder according to the method of Damerval et al. (Electrophoresis 7, 52–54, 1986). The coffee proteins are then extracted from 10 mg of this powder which is solubilized in 100 μl of solution containing 3% w/v of CHAPS, 8.5 M urea, 0.15% w/v of DTT and 3% v/v of ampholyte support pH 3–10.

The mixture is then centrifuged at 13,000 g for 5 min and the supernatant which contains the total proteins of the coffee beans is recovered.

A one-dimensional electrophoresis is performed on this supernatant on the basis of a pH gradient, using, for example, the Multiphore system (Pharmacia Biotech AB, Björkgatan 30, 75182 Upsula, Sweden). To do this, 50 μl are deposited/electrophoresis gel.

To separate the total proteins according to their molecular weights, a second SDS-PAGE electrophoresis is then performed on the gels derived from the first electrophoresis, using, for example, a Bio-Rad equipment (Bio-Rad Laboratories, 2000 Alfred Nobel Drive, Hercules, Calif. 94547 USA) under standard conditions, according to the Laemmli method (Nature, 277, 680–688, 1970). To do this, the gels derived from the one-dimensional electrophoresis are equilibrated with 5 ml/gel of Tris buffer containing 6 M urea, 30% v/v of glycerol, 2% w/v of SDS, 2% w/v of DTT and 2.5% w/v of iodoacetamide, they are placed on the gels of the second SDS-PAGE electrophoresis, and the migration of the proteins is carried out in a Bio-Rad equipment at 40 mA and at a temperature of 12° C. for 9 h, for example.

The gels thus produced are silver stained by the Bjellqvist et al. method (Electrophoresis, 14, 1357–1365, 1993).

The images are then analysed with the aid of a scanner (Scanner XRS 12CX, X-Ray Scanner Corporation, 403 Spencer Street, Torrance, Calif. 90503 USA) and, for example, with the aid of the Bio Image programme (Bio Image, 777 East Eisenhower Parkway, Suite 950, Ann Arbor, Mich. 48108, USA).

The proteins separated by two-dimensional electrophoresis are transferred onto PVDF membranes in a CAPS buffer, with the aid of a Bio-Rad Transblot Cell (Bio-Rad, USA) maintained at 420 mA and at a temperature of 4° C. for 1 h 30 min, and then they are stained with coomassie blue, according to the instructions of Applied Biosystems (Applied Biosystems Inc., 850 Lincoln Centre Drive, Foster City, Calif. 94404 USA).

After the transfer, the membranes are dried at room temperature, before storing them at −18° C. in plastic pouches.

Microsequencing of the N-terminal sequences of the protein blots is carried out with the aid of a sequencer of the Beckman LF 3000 type and of the Beckman Gold HPLC system (Beckmann Instruments Inc., 250 Harbor Boulevard Box 3100, Fullerton, Calif. 92634 USA). For that, the protein blots are cut out of the membrane and subjected to trypsin digestion at pH 8.3 in 50 µl of digestion buffer containing 10% v/v of trypsin, 100 mM of Tris HCl, 1% v/v of triton RTX and 10% v/v of acetonitrile.

The peptides are then separated by HPLC in a C18 column (Merk KGAA Frankfurte Strasse 250, 64923 Darmstadt, DE), using a water/acetonitrile gradient containing 0.05% of TFA, the peptide fractions are concentrated and they are rediluted in 30% of acetonitrile and 0.01% of TFA, and they are sequenced as described above.

The two-dimensional electrophoretic profile, under denaturant conditions of the endosperm of ripe *C. arabica* beans shows 4 groups of proteins which are represented in particular, these proteins having an apparent molecular weight of the order of 70, 56, 32 and 23 kDa.

It can be observed that 2 proteins of the group of proteins at 23 kDa as well as 2 proteins of the group of proteins at 70 kDa have an N-terminal sequence which is identical to the N-terminal sequence of the cleavage protein β.

Furthermore, the fact that 3 proteins of the group of proteins at 32 kDa and 1 protein of the group of proteins at 56 kDa have an N-terminal sequence identical to the N-terminal sequence of the cleavage protein α was demonstrated.

It was also possible to establish 7 internal sequences, of 5 to 15 amino acids, from one of the proteins of 32 kDa.

Moreover, with the aid of the SwissProt databank (Genetics Computer Group Inc., University Research Park, 575 Science Drive, Madison, Wis. 53711 USA) and using the FASTA programme (Pearson and Lipman, Proc. Natl. Acad. Sci. USA, 85, 2444–2448, 1988), it was possible to demonstrate the fact that the N-terminal sequences of the proteins of 23, 32, 56 and 70 kDa and the internal sequences of the protein at 32 kDa have a high homology with the sequences of storage proteins of certain plant species, such as for example glycinins of *Glycine max*, 12s proteins of *Arabidopsis thaliana*, cruciferin of *Brassica napus*, glutelins of *Oryza sativa* and 11s protein of *Cucurbita maxima*.

In the light of these results, it has been possible to make the following hypotheses on the structure of the storage proteins derived from the coffee bean.

The group of proteins of 56 kDa represents a large precursor, the mature storage protein αβ, comprising two domains, the α domain and the β domain. The two-dimensional electrophoretic profile also demonstrates the existence of the cleavage protein α, present in several isoforms at 32 kDa and that of the cleavage protein β, present in several isoforms at 23 kDa. Thus, like the storage protein αβ, the cleavage proteins α and β may exist in various isoforms. Finally, the group of proteins of 70 kDa represents the trimeric form of the cleavage protein β. Furthermore, the existence of a fragment of the cleavage protein α of 13 kDa has been demonstrated on the two-dimensional electrophoretic profile.

II. Estimation of the Quantity of Storage Proteins Contained in the Coffee Bean and Specificity of Expression of the Storage Proteins Derived From the Coffee Bean The quantity of storage proteins contained in the coffee bean is calculated, in per cent, relative to the total integrated intensity of the two-dimensional electrophoretic profile. To do this, the integrated intensity of the protein blots, representing the storage protein αβ, the cleavage protein α, the cleavage protein β, the trimeric form of the cleavage protein β and the fragment of the cleavage protein α is measured.

It is accepted that the total integrated density of the two-dimensional electrophoretic profile is equivalent to 100%.

A value of 50% of storage proteins contained in the coffee bean is thus obtained.

Moreover, the expression of the storage proteins of the coffee bean in tissues of the coffee bean other than the endosperm is also checked by two-dimensional electrophoresis. It is thus possible to demonstrate the fact that the storage proteins are only synthesized in a large quantity in the endosperm and in a much lower proportion in the embryo of the coffee bean.

III. Isolation and Translation in Vitro of the PolyA+ messengers RNAs From the Total RNAs of the Coffee Bean The total RNAs are extracted from coffee beans harvested from 4 to 40 weeks after flowering.

To do this, the maternal tissues are separated from the coffee beans which are rapidly ground in liquid nitrogen before being reduced to a powder.

This powder is then resuspended in 8 ml of buffer at pH 8 containing 100 mM Tris-HCl, 0.1% w/v of SDS and 0.5% v/v of β-mercaptoethanol, it is homogenized with one volume of phenol saturated with 100 mM Tris-HCl, pH 8, and then centrifuged at 12,000 g for 10 min at 4° C., so as to extract the aqueous phase which is centrifuged (i) once with an equivalent volume of phenol, (ii) twice with an equivalent volume of phenol:chloroform (1:1) and (iii) twice with an equivalent volume of chloroform.

The total nucleic acids are then precipitated for 1 h at −20° C. by adding to the aqueous phase 1/10 of the volume of 3 M sodium acetate, pH 5.2 and 2.5 volumes of ethanol.

The whole is then centrifuged at 12,000 g for 30 min at 4° C. and the pellet is taken up in 10 ml of $H_2O$, before precipitating the nucleic acids again in the presence of LiCl (2 M final) and ethanol (2.5 volumes).

After centrifugation, the pellet of total RNAs is taken up in 1 ml of $H_2O$ and it is digested for 1 h at 37° C. with DNAse RQ1 (Promega Corporation, 2800 Woods Hollow Road, Madison, Wis. 53711 USA), so as to eliminate any trace of DNA, and the total RNAs are then deproteinized by treatment with phenol and with chloroform, before precipitating them in the presence of sodium acetate as described above.

The total RNAs are then taken up in 500 µl of $H_2O$ and they are quantified by spectrophotometric assay at 260 nm. Their quality is analysed by agarose gel electrophoresis in the presence of formaldehyde and by in vitro translation.

To do this, the polyA+ messenger RNAs(mRNA) are then purified from 500 µg of total RNAs using the Oligotex-dT purification system (Qiagen INC., 9600 De Soto Avenue, Chatsworth, Calif. 91311 USA), and the quality of the mRNAs is then evaluated by their capacity to synthesize proteins in vitro. For that, translation experiments are carried out with 1 µg of mRNA in the presence of a rabbit reticulocyte lysate (Promega, USA), and then the proteins thus synthesized are labelled by incorporation of $^{35}$S-methionine (Amersham International plc., Amersham Place, Little Chalfont, Buckinghamshire HP7 9NA, UK). The labelled proteins are then separated by two-dimensional electrophoresis as described above. After fixing in an acetic acid/ethanol mixture (40/10), the gels are incubated in the presence of Amplify (Amersham, UK), they are dried under vacuum and they are exposed at −80° C. against an autoradiographic film.

On the one hand, the results of the in vitro translations with the mRNAs extracted from beans 4 to 40 weeks old after flowering demonstrate the presence of numerous proteins with molecular weights of between 1 and 100 kDa.

On the other hand, the results of the in vitro translations with the mRNAs extracted from beans harvested between 16 and 30 weeks after flowering demonstrate the presence, in a large quantity, of proteins which correspond to the αβ form of the storage proteins. On the other hand, no product of translation corresponding in size to the cleavage proteins α and β is observed. This result confirms the hypothesis made above, according to which these-two cleavage proteins are effectively derived from the in vivo cleavage of the large αβ precursor.

To isolate the cDNA for these storage proteins, two libraries were made in the manner described below.

IV. Construction and Screening of cDNA Libraries

The synthesis of cDNA, necessary for the construction of libraries, is carried out according to the recommendations provided in the "Riboclone cDNA synthesis system M-MLV (H—)" kit (Promega, USA), using the mRNA extracted from coffee beans harvested 16 and 30 weeks after flowering. The efficiency of this reaction is monitored by the addition of [alpha-$^{32}$P] dCTP during the synthesis of the two DNA strands.

After migration on an alkaline agarose gel (Sambrook et al., Molecular Cloning—A Laboratory Manual, 1989), the size of the new synthesized cDNA is estimated to vary from 0.2 to more than 4.3 kb. The quantifications, with the aid of the DNA Dipstick kit (InVitrogen BV, De Schelp 12, 9351 NV Leek, Netherlands), show that about 100 ng of cDNA are synthesized from 1 µg of mRNA.

The new synthesized cDNA(s) are then treated according to the recommendations provided in the RiboClone EcoRI Adaptator Ligation System kit (Promega, USA) and they are ligated into the plasmid pBluescript II: SK (+) (Stratagene, 11011 North Torrey Pines Road, La Jolla, Calif. 92037, USA) previously digested with the restriction enzyme EcoRI and dephosphorylaced by treatment with calf intestinal alkaline phosphatase.

The whole of this ligature mixture is used to convert the E. coli strain XL1-Blue MRF' (Stratagene, USA). The bacteria containing recombinant vectors are selected on dishes with LB (Luria-Bertani) medium containing 12.5 µl/ml of tetracycline, 20 µg/ml of ampicillin, 80 µg/ml of methicillin and in the presence of IPTG and X-Gal (Sambrook et al., 1989). They are then cultured on Petri dishes so as to obtain about 300 clones per dish. These clones are transferred onto Nylon filter and they are then treated according to the recommendations provided by Boehringer Mannheim (Boehringer Mannheim GmbH, Biochemica, Postfach 310120, Mannheim 31, DE).

Moreover, the sequence from amino acids 325 to 330 of the sequence SEQ ID NO: 2 is chosen in the amino acid sequence of the cleavage protein β because it makes it possible to designate an oligonucleotide probe which is relatively only slightly degenerate, the probe OLIGO 1, having the nucleic sequence SEQ ID NO: 4, which is labelled at its 5' end by the addition of the digoxigenin radical (Genosys Biotechnologies Inc., 162A Science Park, Milton Road, Cambridge CB4 4BR, UK).

The filters are prehybridized at 65° C. for 4 h in the hybridization solution defined in the DIG oligonucleotide 3'-end labelling kit protocol (Boehringer Mannheim, DE) and the hybridization is carried out at 37° C. for 10 h in the presence of the probe OLIGO1 (10 pmol/ml final).

After the hybridization, the filters are washed in the presence of tetramethylammonium chloride according to the protocol defined by Wood et al. (Proc. Natl. Acad. Sci. USA, 82, 1585–1588, 1985) and then they are subjected to immunological detection in the presence of CSPD (Tropix, 47 Wiggins Avenue, Bedford, Mass. 01730 USA) according to the recommendations provided by Boehringer Mannheim (DIG luminescent detection kit).

A positive clone harbouring the recombinant vector, called "pCSP1" in the remainder of the description, is selected from the screening of the cDNA library carried out 16 weeks after flowering. This vector contains a cDNA, cloned into the EcoRI site of the vector pBluescript II SK (+), which is sequenced according to the "T7 sequencing kit" protocol (Pharmacia, Sweden) in the presence of [alpha-$^{35}$S] DATP. This cDNA comprises the last 819 nucleotides of the sequence SEQ ID NO: 1 and, consequently, is incapable of encoding the storage protein αβ.

To isolate the cDNA encoding the entire storage protein αβ, a new nucleic probe, called So1 in the remainder of the description, is synthesized. To do this, a PCR is carried out (U.S. Pat. No. 4,683,195 and U.S. Pat. No. 4,683,202)using the synthetic oligonucleotide OLIGO 2, having the nucleic sequence SEQ ID NO: 5, and the synthetic olignucleotide OLIGO 3, having the nucleic sequence SEQ ID NO:6.

The PCR reaction is carried out in the presence of 0.1 ng of vector pCSP1, in a final volume of 50 µl containing 50 mM KCl, 10 mM Tris-HCl, pH 8.8, 1.5 mM $MgCl_2$, 0.1 mg/ml gelatin, 0.2 mM of each DNTP, 0.25 µM of each oligonucleotide (OLIGO 2 and OLIGO*3) and 3 units of Taq DNA polymerase (Stratagene, USA). The reaction mixture is covered with 50 µl of mineral oil and it is incubated for 30 cycles (94° C.-30 s, 42° C.-30 s, 72° C.-2 min) followed by a final extension at 72° C. for 7 min. The fragment obtained after amplification is purified on a Microcon 100 cartridge (Amicon INC, 72 Cherry Hill Drive, Beverly, Mass. 01915 USA) and 50 ng of this fragment are labelled by random primer extension with 50 μCi of [alpha-$^{31}$p] dCTP according to the Megaprime kit (Amersham, UK).

Furthermore, the Nylon filters used during the screening with the probe OLIGO 1 are dehybridized by two washes of 15 min at 37° C., in the presence of 0.2 N-NaOH-0.1% SDS (w/v) and then prehybridized for 4 h at 65° C. in a solution containing 6×SSC, 1×Denhart (0.2% Ficoll, 0.2% polyvinylpyrrolidone, 0.2% BSA fraction IV) and 50 μg/ml of denatured salmon sperm DNA. They are then hybridized for 10 h at 65° C. in the same solution with the whole of the labelled probe SO1 and then they are washed for 30 min at 65° C. three times in the presence, successively, of 2×SSC-0.1% SDS, 1×SSC-0.1% SDS and 0.1×SSC-0.1% SDS.

A positive clone harbouring the recombinant vector, called in the remainder of the description pCSP2 is thus selected from the screening of the cDNA library carried out at 30 weeks after flowering. This vector contains the sequence SEQ ID NO: 1 of 1706 bp, corresponding to the cDNA encoding the entire storage protein αβ, having as amino acid sequence the sequence SEQ ID NO: 2 and a theoretical molecular weight of 54999 Da. A search of the SwissProt databank with the sequence SEQ ID NO: 2 confirms that this coffee protein belongs to the family of type 11s plant storage proteins.

The cleavage site of the precursor is located between amino acids 304 and 305 of the amino acid sequence SEQ ID NO: 2, as has been observed for all the other type 11s plant proteins (Borroto and Dure, Plant Mol. Biol. 8, 113–131, 1987). This is also confirmed by the N-terminal sequencing of the cleavage protein β described above. Consequently, the cleavage protein α corresponds to the first 304 amino acids of the amino acid sequence SEQ ID NO: 2, whereas the cleavage protein β corresponds to the last 188 amino acids of this sequence. The theoretical molecular weights of α and β are respectively 34125 Da and 20892 Da and are in agreement with those described above under "Identification of the storage proteins of the coffee bean".

The N-terminal sequences of the cleavage proteins α and β analysed above are found in the amino acid sequence SEQ ID NO: 2 with the exception of a few amino acids. These differences are probably explained by the existence of several isoforms of these proteins which may differ from each other by a few amino acids (Shirsat, Developmental Regulation of Plant Gene Expression, Grierson Ed., Blackie, Chapman and Hall NY, 153–181, 1991).

V. Expression of the Gene Encoding the Storage Protein αβ During the Development of the *Coffea Arabica* Bean The expression of the gene encoding the storage protein αβ in coffee beans harvested at various stages of development (at 9, 12, 16, 30 and 35 weeks after flowering) is monitored.

To do this, 10 μg of total RNAs of these coffee beans are denatured for 15 min at 65° C. in 1×MOPS buffer (20 mM MOPS, 5 mM sodium acetate, 1 mM EDTA, pH 7) in the presence of formamide (50%) and formaldehyde (0.66 M final).

They are then separated by electrophoresis, for 6 h at 2.5 V/cm, in the presence of 1×MOPS buffer, on a 1.2% agarose gel containing 2.2 M formaldehyde as final concentration.

After migration, the RNAs are stained with ethidium bromide (BET) according to Sambrook et al. 1989, which makes it possible to standardize the quantities deposited on a gel from the intensities of fluorescence of the 16S and 23S ribosomal RNAs.

The total RNAs are then transferred and fixed on a positively charged Nylon membrane according to the recommendations provided by Boehringer Mannheim (Boehringer Mannheim, DE). The prehybridization and hybridization are carried out according to the conditions described above in chapter IV.

The mRNAs encoding the storage protein αβ are completely absent from the beans harvested up to 9 weeks after flowering. They begin to be very weakly detected in the beans harvested at 12 weeks after flowering and are very abundant in the beans harvested between 16 and 30 weeks after flowering, again becoming very weakly represented in the ripe coffee beans (35 weeks after flowering). In all cases, the probe SO1 hybridizes with only one class of mRNA whose estimated size at around 1.8 kb is close to that of the nucleic sequence SEQ ID NO: 1.

The kinetics of accumulation of the mRNAs is similar to that observed for most of the genes for storage proteins (Shirsat, 1991). According to the tissue examinations made during the maturation of the coffee beans, it is observed that the increase in the quantity of mRNA between 12 and 16 weeks after flowering occurs at the same time as the absorption of the perisperm by the endosperm. In comparison with the analyses carried out above by two-dimensional electrophoresis, on the accumulation of proteins during the maturation of the bean, a perfect superposition of the kinetics of accumulation of mRNAs with that of the storage proteins is observed. At the mature stage, the persistence of the storage proteins in the absence of their corresponding messenger RNAs is explained by a high stability of these proteins in vivo. According to these observations, and as has been shown in other plant species (Shirsat, 1991) it appears that the expression of the gene encoding the storage protein αβ is essentially controlled by a promoter, a sequence capable of regulating the transcription of the gene, which is specifically expressed in the endosperm of the coffee beans.

VI. Isolation of the Promoter of the Gene Encoding the Storage Protein αβ of *Coffea Arabica*

The promoter of the gene encoding the storage protein αβ of *Coffea arabica* is isolated by several inverse PCRs according to the method of Ochman et al. (Genetics 120, 621–623, 1988).

To do this, the nuclear DNA of coffee is isolated from young leaves of *C. arabica*, Caturra variety, according to the protocol described by Rogers and Bendich (Plant Mol. Biol. Manuel, Gelvin, Schilperoort and Verma Eds, Kluwer Academic Publishers Dordrecht, Netherlands, A6, 1–11, 1993).

0.5 to 1 μg of this DNA is digested with several restriction enzymes, such as for example DraI, HincII and NdeI, and then treated with phenol:chloroform (1:1) and it is precipitated for 12 h at −20° C. in the presence of sodium acetate 0.3 M final and of ethanol (2.5 volumes).

After centrifugation at 10,000 g for 15 min at 4° C., the DNA is taken up in about 500 μl of ligation buffer containing 30 mM Tris-HCl, pH 7.8, 10 mM MgCl$_2$, 10 mM DTT and 0.5 mM rATP, so as to obtain a final DNA concentration of about 1 to 2 ng/μl. The ligation is carried out for 12 h at 14° C. in the presence of T4 DNA ligase at 0.02 Weiss u/μl and then the self-ligated genomic DNA is precipitated as described above and it is taken up in 20 μl of H$_2$O before quantifying it with the DNA Dipstick kit (InVitrogen, Netherlands).

a) Inverse PCR Reaction No. 1

This first reaction is carried out using the synthetic oligonucleotide Solo, having the nucleic sequence SEQ ID NO: 7, and the oligonucleotide SO11, having the nucleic sequence SEQ ID NO: 8.

This inverse PCR reaction is carried out in the presence of 50 ng of ligated genomic DNA in a final volume of 50 µl containing 50 mM KCl, 10 mM Tris-HCl, pH 8.8, 1.5 mM $MgCl_2$, 0.1 mg/ml of gelatin, 0.2 mM of each DNTP, 0.25 µM of each oligonucleotide (SO10 and SO11) and 3 units of Taq DNA polymerase (Stratagene, USA). Next the reaction mixture is covered with 50 µl of mineral oil and it is incubated for 30 cycles (94° C.-30 s, 56° C.-30s, 72° C.-3 min) followed by a final extension cycle at 72° C. for 7 min.

The amplified DNA fragments are then analysed by molecular hybridization (J. Southern, Mol. Biol. 98, 503–517, 1975), they are separated by electrophoresis on 1% agarose gel stained with ethidium bromide and then they are transferred in the presence of 0.4 N NaOH for 12 h onto positively charge Nylon membrane (Boehringer Mannheim, DE).

After the transfer, the membrane is baked for 15 min at 120° C. and then it is prehybridized at 65° C. for 4 h in the hybridization solution defined in the "DIG oligonucleotide 3'-end labelling kit" protocol (Boehringer Mannheim, DE).

The membrane is then hybridized at 37° C. for 10 h in the presence of the synthetic oligonucleotide SO12 (10 pmol/ml), having the nucleic sequence SEQ ID NO: 9 and labelled at its 5' end with a digoxigenin radical.

After hybridization, the filters are washed in the presence of tetramethylammonium chloride according to the protocol defined by Wood et al., 1985, and then they are subjected to immunological detection in the presence of CSPD (Tropix, USA), according to the recommendations provided in the DIG luminescent detection kit (Boehringer Mannheim, DE).

After autoradiography, the presence of a DNA fragment of about 1.7 kb, derived from the inverse PCR reaction on the genomic DNA initially digested with the restriction enzyme HincII, which binds the probe SO12, is detected.

This DNA is then cloned into the vector pCR-Script (SK+) (Stratagene, USA). To do this, 10 µl of the inverse PCR reaction are mixed with 100 µl of sterile water and then the mixture is centrifuged for 10 min at 3000 g in a Microcon 100 cartridge (Amicon, USA).

3 µl of the DNA thus purified are treated in the presence of native Pfu DNA polymerase (Stratagene, USA) in order to convert its cohesive ends to blunt ends. This reaction is carried out in a final volume of 10 µl containing 10 mM KCl, 6 mM $(NH_4)_2SO4$, 20 mM Tris-HCl, pH 8.0, 0.1% Triton X-100, 2 mM $MgCl_2$, 1 mM of each dNTP, 10 µg/ml BSA and the reaction mixture is covered with 50 µl of mineral oil, it is incubated for 30 min at 72° C. and then 1 µl of this reaction mixture is directly used in the ligation reaction with the vector pCR-Script SK(+).

The whole of this ligation mixture (10 µl) is used to transform the E.coli strain XL1-Blue MRF' (Stratagene, USA). The bacteria containing the recombinant vectors are selected on dishes with LB medium containing 20 µg/ml of ampicillin, 80 µg/ml of methicillin and in the presence of IPTG and X-Gal (Sambrook et al., 1989).

At the end of the transformation, about 100 clones are obtained which are transferred onto Nylon filter and are analysed by molecular colony hybridization (Grunstein and Hogness, Proc. Natl. Acad. Sci. USA 72, 3961–3965, 1975) with the probe S012 according to the conditions described above. This screening makes it possible to isolate a positive clone harbouring the recombinant vector pCSPP1. This vector contains the genomic DNA fragment detected by autoradiography which is cloned into the SfrI site of the vector pCR-Script (SK+). This DNA is sequenced, according to the protocol defined by Pharmacia (T7 sequencing kit), in the presence of [alpha-$^{35}$S] dATP. It comprises the last 1717 base pairs of the nucleic sequence SEQ ID NO: 3, bordered at each end by an HincI restriction site. It contains 750 base pairs upstream of the codon for initiation of translation of the gene encoding the storage protein αβ and the first 968 base pairs of this nuclear gene. Given the fact that this gene belongs to a multigene family, it will be called hereinafter CSP1.

This partial sequence of the CSP1 gene shows the presence of two introns of identical size (111 bp), located respectively between nucleotides 2811–2921 for the first, and nucleotides 3239–3349 for the second nucleic sequence SEQ ID NO: 3. These two introns have sizes less than those observed, for example, in *Arabidopsis thaliana* but they are on the other hand located at the same positions as those observed in this plant (Pang et al., Plant Mol. Biol 11, 805–820).

b) Inverse PCR Reaction No. 2: First Screening

To obtain the nucleic sequences located upstream of the HincII site (position 1763 of the nucleic sequence SEQ ID NO: 3, another inverse PCR reaction is carried out using, this time, the synthetic oligonucleotides SO16 and SO17 deduced from the sequence previously cloned to the plasmid pCSPP1 and having respectively the nucleic sequences SEQ ID NO: 10 and SEQ ID NO: 11.

This inverse PCR reaction is carried out under conditions identical to those described for the inverse PCR reaction No. 1, with the exception of the following parameters: the attachment of the oligonucleotides was carried out at 57° C. and 35 polymerization cycles were performed.

As defined above, the DNA fragments amplified by this PCR are analysed by molecular hybridization after having been separated on an electrophoresis gel and they are transferred onto a Nylon membrane. This membrane is then prehybridized for 4 h at 65° C. in a solution containing 6×SSC, 1×Denhart (0.2% Ficoll, 0.2% polyvinylpyrrolidone, 0.2% BSA fraction IV) and 50 µg/ml of denatured salmon sperm DNA and then it is hybridized for 10 h at 65° C. in the same solution with the probe SO1016.

This probe is in fact synthesized by PCR using the synthetic oligonucleotides SO10 and SO16 described above, in the presence of 0.1 ng of vector pCSPP1, in a final volume of 50 µl containing 50 mM KCl, 10 mM Tris-HCl, pH 8.8, 1.5 mM $MgCl_2$, 0.1 mg/ml gelatin, 0.2 mM of each dNTP, 0.25 µM of each oligonucleotide (SO10 and SO16) and 3 units of Taq DNA polymerase (Stratagene, USA). The reaction mixture is covered with 50 µl of mineral oil and it is incubated for 30 cycles (94° C.-30 s, 46° C.-30 s, 72° C.-2 min) followed by a final extension cycle at 72° C. for 7 min. The fragment obtained after amplification (698 bp) is purified on a Microcon 100 cartridge (Amicon, USA) and 50 ng of this fragment are labelled by random primer extension with 50 µci of [alpha-$^{32}$P] dCTP according to the Megaprime kit (Amersham, UK) protocol.

After hybridization, the membrane is washed three times for 30 min at 65° C. in the presence, successively, of 2×SSC-0.1% SDS, 1×SSC-0.1% SDS and 0.1×SSC-0.1% SDS and it is analysed by autoradiography so as to detect a DNA fragment of about 1 kb which binds the probe SO1016.

This DNA, derived from the inverse PCR reaction on the genomic DNA initially digested with the restriction enzyme NdeI, is then treated with Pfu DNA polymerase and then it is ligated into the vector pCR-Script(SK+) as described above. This ligation is then used to transform the E.coli strain XL1-Blue MRF' and the transformants are selected and analysed by molecular hybridization with the probe SO1016 according to the conditions described above. This screening makes it possible to isolate a positive clone harbouring the vector pCSPP2. As expected, this vector results from the cloning into the SfrI site of the vector pCR-Script (SK+) of the DNA fragment previously identified by hybridization. The latter, which corresponds to the DNA segment between nucleotides 1514 and 2523 of the nucleic sequence SEQ ID NO: 3, bordered at each of the ends by an NdeI restriction site and which consequently contains 250 bp in addition upstream of the genomic DNA fragment cloned into the vector pCSPP1, is sequenced.

c) Inverse PCR Reaction No. 2: Second Screening

To clone nucleotides 1 to 1513 of the nucleic sequence SEQ ID NO: 3, another molecular hybridization is performed on the DNA fragments derived from the inverse PCR reaction No. 2.

To do this, the probe used, called SO1720, is deduced from the sequence of coffee nuclear DNA cloned into the vector pCSPP2 and it is synthesized by PCR using the oligonucleotide SO17 described above and the oligonucleotide SO20 having the nucleic sequence SEQ ID NO: 12. This reaction is carried out in the presence of 0.1 ng of vector pCSPP2, under conditions identical to those used for the synthesis of the probe SO1016, with the exception of the temperature for attachment of the oligonucleotides which is 50° C. The fragment obtained after amplification (262 bp) is labelled as described above and it is used as probe to test the inverse PCR reactions No. 2.

The Nylon membrane used during the screening of the products of the inverse PCR reaction No. 2 with the probe SO1016 is dehybridized by two washes for 15 min at 37° C. in the presence of 0.2 N NaOH-0.1% SDS (w/v), then it is prehybridized and it is hybridized as described above with the probe SO1720.

At the end of this hybridization, a DNA fragment of about 1.9 kb, derived from the inverse PCR reaction No. 2 on the genomic DNA initially digested with the restriction enzyme DraI, is detected. As described above, this DNA is then treated with Pfu DNA polymerase, it is ligated into the vector pCR-Script (SK+) and the entire ligation is used to transform the E.coli strain XL1-Blue MRF'.

The transformants are then selected and they are screened by molecular hybridization with the probe SO1720. It is thus possible to isolate a positive clone harbouring the vector pCSPP3 which results from the cloning into the SfrI site of the vector pCR-Script (SK+) of the DNA fragment previously identified by hybridization. The latter, which corresponds to the DNA segment between nucleotides 1 and 1886 of the nucleic sequence SEQ ID NO: 3, bordered at each end by a DraI restriction site, is sequenced. It therefore contains 1513 base pairs in addition upstream of the genomic DNA fragment cloned into the vector pCSPP2.

d) Cloning of the Genomic DNA Fragments

The inverse PCR experiments form chimeric linear molecules by combining noncontiguous DNA fragments in the genome with each other (Ochman et al., 1988). Moreover, measurements of mutation frequency show that the Pfu DNA polymerase is approximately twelve times more accurate than Taq DNA polymerase, which reduces the probability of point mutations during PCR amplifications (Lundberg et al., Gene 108, 1–6, 1991).

For these reasons, a PCR reaction is carried out on the native genomic DNA of C. arabica, Caturra variety, in the presence of Pfu DNA polymerase. This reaction is carried out in the presence of 10 ng of genomic DNA, in a final volume of 50 µl containing 10 mM KCl, 6 mM $(NH_4)_2SO_4$, 20 mM Tris-HCl, pH 8.0, 0.1% Triton X-100, 2 mM $MgCl_2$, 10 µg/ml BSA, 0.2 mM of each dNTP, 0.25 µM of the oligonucleotides, SO10 and SO20 described above and 3 units of Pfu DNA polymerase. The oligonucleotide SO10 is located on the antisense strand of the nucleic sequence SEQ ID NO: 3, between nucleotides 2512 and 2534 whereas the oligonucleotide SO20 is located on the sense strand of the nucleic sequence SEQ ID NO: 3, between nucleotides 1565 and 1584. The reaction mixture is then covered with 50 µl of mineral oil and it is incubated for 45 cycles (94° C.-30 s, 50° C.-30 s, 72° C.-3 min) followed by a final extension cycle at 72° C. for 7 min.

Following this PCR, a single fragment is obtained which is cloned into the vector pCR-Script (SK+) to give the vector pCSPP4. By sequencing, it is shown that this genomic DNA fragment corresponds to the sequence between oligonucleotides SO10 and SO20. The DNA amplified during this PCR reaction is then used for the construction of the vectors, as described below.

VII. Construction of the Genetic Transformation Vectors Necessary for the Functional Analysis of the Promoter of the Gene Encoding the Storage Protein αβ of Coffea Arabica The sequences located upstream of the site of initiation of translation, positioned at 2510 of the nucleic sequence SEQ ID NO: 3, are analysed in order to test their capacity for regulating the expression of the reporter gene uida, in the beans of transformed plants.

To do this, several constructs are made in the binary transformation vector pBI101 (Clontech Laboratories Inc., 1020 East Meadow Circle, Palo Alto, Calif. 94303–4230 USA). This vector contains the reporter gene uida which encodes β-glucuronidase (GUS) and the bacterial gene nptII, which encodes neomycin phosphotransferase. The latter confers resistance to kanamycin in the transformed plants. These two genes are bordered by the right and left ends of the T-DNA of the plasmid pTiT37 of Agrobacterium tumefaciens (Bevan, Nucl. Acids Res. 12, 8711–8721, 1984) which define the DNA region capable of being transferred into the genome of plants infected with this bacterium.

The vector pBI1010 is digested with the restriction enzyme BamHI and it is dephosphorylated by treatment with calf alkaline phosphatase (Promega, USA) according to the protocol defined by the supplier.

Next, DNA fragments of different size which are obtained by PCR in the presence of the vector pCSPP4, of Pfu DNA polymerase and of two synthetic oligonucleotides each containing at their 5' end the nucleic sequence SEQ ID NO: 13, are cloned into the vector PBI101. This sequence comprises a BamHI restriction site which allows the cloning of the PCR products into the vector pBI101 linearized with the same enzyme.

A synthetic oligonucleotide is used, on the one hand, which is capable of binding to the promoter and, on the other hand, the oligonucleotide BAGUS which has the nucleic sequence SEQ ID NO: 14. The use of the latter allows, after digestion of the PCR products with the restriction enzyme BamHII, a translational fusion between the first 5 amino acids of the storage protein αβ of the coffee bean and the N-terminal end of β-glucuronidase to be obtained.

a) Construction of pCSPP5

The PCR reaction is carried out with 5 ng of plasmid pCSPP4, in a volume of 50 µl containing 10 mM KCl, 6 mM ($NH_4)_2SO_4$, 20 mM Tris-HCl, pH 8, 0.1% Triton X-100, 2 mM $MgCl_2$, 0.2 mM of each dNTP, 10 µg/ml BSA, 0.25 µM of the oligonucleotide UP210 having the nucleic sequence SEQ ID NO: 15 and BAGUS, having the nucleic sequence SEQ ID NO: 14, and 3 units of Pfu DNA polymerase. The reaction mixture is covered with 50 µl of mineral oil and it is incubated for 30 cycles (94° C.-30 s, 55° C.-30 s, 72° C.-2 min) followed by a final extension cycle at 72° C. for 7 min.

The PCR fragment of about 950 bp is purified on a Microcon 100 cartridge (Amicon, USA), and it is digested for 12 h at 37° C. with BamHI (Promega, USA) and it is ligated into the linearized vector pBI101, in the presence of T4 DNA ligase (Promega, USA), according to the recommendations provided by the supplier. Next, the E. coli strain XL1-Blue MRF' is transformed with the entire ligation mixture. The plasmids are independently extracted from several transformants and they are sequenced so as to determine the orientation of the PCR fragment in the binary vector. This analysis thus makes it possible to select the plasmid pCSPP5.

b) Construction of pCSPP6

The construction of this vector is carried out as described for the vector pCSPP5 except for the fact that the oligonucleotide UP210 is replaced with the oligonucleotide UP211 which has the nucleic sequence SEQ ID NO: 16. The cloning of the PCR product (about 700 bp), correctly oriented in the vector pBI101, gives the vector pCSPP6.

c) Construction of pCSPP7

The construction of this vector is carried out as described for the vector pCSPP5 except for the fact that the oligonucleotide UP210 is replaced with the oligonucleotide UP212 which has the nucleic sequence SEQ ID NO: 17. The cloning of the PCR product (450 bp), correctly oriented in the vector pBI101, gives the vector pCSPP7.

d) Construction of pCSPP8

The construction of this vector is carried out as described for the vector pCSPP5 except for the fact that the oligonucleotide UP210 is replaced with the oligonucleotide UP213 which has the nucleic sequence SEQ ID NO: 18. The cloning of the PCR product (250 bp), correctly oriented in the vector pBI101, gives the vector pCSPP8.

VIII. Transformation of *Agrobacterium tumefaciens*

The vectors described above (pCSPP5–8), as well as the plasmids pBI101 and pBI121 (Clontech) are independently introduced into the disarmed *Agrobacterium tumefaciens* strain C58pMP910 (Koncz and Schell, Mol. Gen. Genet. 204, 383–396, 1986) according to the direct transformation method described by An et al. (Plant Mol. Biol. Manuel, Gelvin, Schilperoort and Verma Eds, Kluwer Academic Publishers Dordrecht, Netherlands, A3, 1–19, 1993). For each transformation, the recombinant *Agrobacterium tumefaciens* clones are selected on LB medium supplemented with kanamycin (50 µg/ml) and rifampicin (50 µg/ml).

To check the structure of the plasmids introduced into *Agrobacterium tumefaciens*, they are extracted by the rapid minipreparation technique described by An et al. (1993) and they are analysed by restriction mapping after reverse transformation in the *E.coli* strain XL1-Blue MRF'.

In the plasmid pBI101, the gene uida is silent because it lacks a promoter. In contrast, this same gene is expressed in plants transformed with the vector pBI121 because it is under the control of the constitutive CaMV 35S promoter (Jefferson et al., J. EMBO, 6, 3901–3907, 1987). These two plasmids were used respectively as negative and positive controls for the expression of the reporter gene uida.

IX. Transformation and Regeneration of *Nicotiana tabacum*

The transformation of *Nicotiana tabacum* var. XHFD8 is carried out with the vectors described above (pCSPP5–8, pBI101 and pBI121), according to the protocol described by Horsch et al. (Plant Mol. Biol. Manuel, Gelvin, Schilperoort and Verma Eds, Kluwer Academic Publishers Dordrecht, Netherlands, A5, 1–9, 1993).

To do this, foliar discs of plantlets which are germinated in vitro are incubated for about 2 min with a transformed stationary phase culture of *Agrobacterium tumefaciens* diluted in a 0.9% NaCl solution so as to obtain an OD measurement at 600 nm of between 0.2 and 0.3. They are then dried on 3 MM paper (Whatmann), they are incubated, without selection pressure, in a culture chamber on MS-stem medium (MS salts 4.3 g/l, sucrose 30 g/l, agar 8 g/l, myoinositol 100 mg/l, thiamine 10 mg/l, nicotinic acid 1 mg/l, pyridoxine 1 mg/l, naphthaleneacetic acid (NAA) 0.1 mg/l, benzyladenine (BA) 1 mg/l) (Murashige and Skoog, Physiol. Plant 15, 473–497, 1962).

After 3 days, the discs are transferred onto MS medium supplemented with kanamycin (100 µg/ml) and with cefotaxime (400 µg/ml) in order to multiply the transformed cells so as to obtain calli. These discs are then subcultured every week on fresh "MS-stem" medium.

After 21 to 28 days, the buds which germinate are cut from the calli and they are subcultured on standard MS medium, that is to say an MS medium free of phytohormones, supplemented with kanamycin (100 µg/ml) and with cefotaxime (200 µg/ml). After rooting on a Petri dish, the plantlets are transplanted into earthenware pots in a substrate composed of peat and compost and then grown in a greenhouse at a temperature of 25° C. and with a photoperiod of 16 h. For each transformation experiment, 30 plantlets (RO generation) are selected. All these plantlets proved to be morphologically normal and fertile. They were selfed and gave seeds (R1 generation).

X. Analysis of the Genomic DNA of Tobacco Plants Transformed With *Agrobacterium tumefaciens*

The genomic DNA of transgenic tobacco plants is extracted from the leaves according to the protocol described by Rogers and Bendich (Plant Mol. Biol. Manuel, Gelvin, Schilpoort and Verma Eds, Kluwer Academic Publishers Dordrecht, Netherlands, A6, 1–11, 1993) and then they are analysed by PCR and by molecular hybridization, according to the Southern-Blot technique.

The PCR reactions are carried out with 10 ng of DNA in a final volume of 50 µl containing 50 mM KCl, 10 mM Tris-HCl, pH 8.8, 1.5 mM $MgCl_2$, 0.1 mg/ml gelatin, 0.2 mM of each dNTP, 3 units of Taq DNA polymerase, 0.25 µM of the oligonucleotide BI104, having the sequence SEQ ID NO: 19 described in the sequence listing hereinafter, and 0.25 µM of the oligonucleotide BI105, having the sequence SEQ ID NO: 20, described in the sequence listing hereinafter. The oligonucleotide BI104 is located at 27 bp downstream of the BamHI site of the plasmid BI101 and the oligonucleotide BI105 is located at 73 bp upstream of the BamHI site of the plasmid pBI101. The PCR reactions are carried out over 30 cycles (94° C.-30 s, 54° C.-30 s, 72° C.-2 min) followed by a cycle of 7 min at 72° C. (final extension). The DNA fragments amplified from transgenic tobacco plants transformed with the plasmids pBI101 (negative control), pBI121 (positive control), pCSPP5, pCSPP6, pCSPP7 and pCSPP8 have molecular weights of about 280 bp, 1030 bp, 1230 bp, 980 bp, 730 bp and 430 bp respectively. In all cases, it is concluded that the fragment initially cloned upstream of the reporter gene uidA is intact.

10 µg of the DNA from tobacco plants transformed with *Agrobacterium tumefaciens* are digested with BamHI. Next, the restriction fragments obtained are separated by electrophoresis on agarose gel (1%) and the DNA is transferred onto a Nylon filter, before hybridizing it independently with a probe uida and a probe nptII.

The probe uida is synthesized by PCR using the synthetic oligonucleotide GMP1, having the sequence SEQ ID NO: 21 described in the sequence listing hereinafter, and the synthetic oligonucleotide GMP2 having the sequence SEQ ID NO: 22 described in the sequence listing hereinafter, in the presence of 0.1 ng of vector pBI101, in a final volume of 50 µl containing 50 mM KCl, 10 mM Tris-HCl, pH 8.8, 1.5 mM $MgCl_2$, 0.1 mg/ml gelatin, 0.2 mM of each dNTP, 0.25 µM of each oligonucleotide and 3 units of Taq DNA polymerase (Stratagene, USA). The reaction mixture is covered with 50 µl of mineral oil and it is incubated for 30 cycles (94° C.-30 s, 46° C.-30 s, 72° C.-2 min) followed by a cycle at 72° C. for 7 min.

The probe nptII is synthesized by PCR using the synthetic oligonucleotide NPTII-1, having the sequence SEQ ID NO: 23 described in the sequence listing hereinafter, and the synthetic olignucleotide NPTII-2 having the sequence SEQ ID NO: 24 described in the sequence listing hereinafter, in the presence of 0.1 ng of vector pBI101, in a final volume of 50 µl containing 50 mM KCl, 10 mM Tris-HCl, pH 8.8, 1.5 mM $MgCl_2$, 0.1 mg/ml gelatin, 0.2 mM of each dNTP, 0.25 µM of each oligonucleotide and 3 units of Taq DNA polymerase (Stratagene, USA). The reaction mixture is covered with 50 µl of mineral oil and it is incubated for 30 cycles (94° C.-30 s, 46° C.-30 s, 72° C.-2 min) followed by a cycle at 72° C. for 7 min.

These two probes are purified and then they are labelled as described above in test VI.

The hybridization profiles obtained for each probe are then compared so as to select the tobacco plants transformed with *Agrobacterium tumefaciens* which have integrated into their genome a single non-rearranged copy of the T-DNA. The selection of these plants is also confirmed by the results of the analysis of the segregation of the kanamycin-resistance character, after germination in vitro on standard MS medium of the R1 seeds of these plants. Indeed, in this case, a ¾-¼ segregation of the kanamycin-resistance character is observed, which is compatible with the integration of the T-DNA at a single locus of the nuclear DNA.

XI. Study of the Functioning Characteristics of the Coffee Promoter and of its Derivatives in Transgenic Tobacco Plants This study is carried out on RO generation plants and on R1 generation mature seeds.

The measurements of the GUS activity are therefore carried out on the leaves and the seeds according to the method described by Jefferson et al. (1987), using MUG (methyl umbelliferyl glucuronide) as substrate and by measuring, by fluorimetry, the appearance of MU (methylumbelliferone). To do this, the foliar explants (10 mg) and the seeds (about 40) are ground in the presence of sterile sand in 300 µl of extraction buffer (50 mM $Na_2HPO_4$, pH 7.0, 10 mM EDTA, 10 mM β-mercaptoethanol). The cellular debris are removed by centrifugation for 15 min at 4° C. and the soluble proteins in the supernatant are quantified by the Bradford method (Anal. Biochem. 72, 248–254, 1976) according to the protocol defined by Bio-Rad (USA) and using BSA as standard. The measurements of GUS activity are carried out in microtitre plates incubated at 37° C., using 1 µg of soluble proteins in 150 µl of reaction buffer (extraction buffer with 1 mM MUG). The measurements of fluorescence, expressed in pmol MU/min/mg of proteins are carried out at an excitation wavelength of 365 nm and an emission wavelength of 455 nm (FluoroskanII, Labsystem).

The results of the measurements of GUS activity which are presented in FIG. 1 hereinafter show that no enyzmatic activity is observed in the leaves and the seeds of the plants containing the T-DNA of the plasmid pBI101. For the other transformation experiments, the differences in GUS activities which are observed between each of the transgenic plants transformed with the same genetic construct can be explained by a positional effect which results from the random integration of the T-DNA into the genome (Jones et al., J. EMBO, 4, 2411–2418, 1985). The plants containing the construct pBI121 have a glucuronidase activity of between 1500 and 20,000 pmol of MU/min/mg of proteins. For these same plants, no significant differences are observed between the measurements of GUS specific activities carried out using the seeds and the leaves. These observations confirm the constitutive character of the CaMV 35S promoter in plants (Odell et al., Nature 313, 810–812, 1985).

Analysis of the results shows that the GUS activities measured in the leaves of the plants independently containing the T-DNAs of the plasmid constructs pCSPP5, pCSPP6, pCSPP7 and pCSPP8 are zero. On the other hand, the GUS activities measured in the seeds of these same plants, independently containing the T-DNAs of the plasmid constructs pCSPP5, pCSPP6, pCSPP7 and pCSPP8, are respectively 60, 60, 30 and 12 times higher than the average GUS activity measured in the seeds of the plants transformed with the plasmid pBI121. It is also observed that the maximum expression of the uida gene is obtained with the vectors pCSPP5 and pCSPP6, reaching on average 465 nmol of MU/min/mg of protein. From this observation, it can be concluded that the DNA fragment between nucleotides 1572 (5' end of the sequence SEQ ID NO: 15) and 1815 (5' end of the sequence SEQ ID NO: 16) of the sequence SEQ ID NO: 3 contains no sequence which is critical in the functioning of the coffee promoter.

The most substantial deletions made in the promoter (corresponding to the vectors pCSPP7 and pCSPP8) have as a consequence a reduction in the level of expression of the uida reporter gene which is greater, the more substantial the deletion. On the other hand, these deletions do not lead in any case to a loss of the specificity of expression of the promoter since in all the transgenic plants analysed, the uida reporter gene continues to be specifically expressed in the seeds. The measurements of the GUS activity show that the coffee DNA sequence between nucleotides 1572 and 2524 of the sequence SEQ ID NO: 3 described in the sequence listing hereinafter effectively contains a promoter which behaves like a very strong promoter in the tobacco seeds compared with the 35S promoter of CaMV. It is also observed that this same DNA sequence, as well as the deletions derived therefrom contain the information which is necessary and sufficient to direct the expression of the uidA reporter gene in the seeds of the transgenic tobacco plants at a level which is in all cases greater than that conferred by the reference promoter CaMV35S.

XII. Expression of the Coffee 11s Storage Protein in *Escherichia Coli*

To overexpress and purify the coffee 11s protein in *Escherichia coli*, a PCR amplification of the DNA sequence between nucleotides 108 and 1517 of the sequence SEQ ID NO: 1 is carried out with the aid of the oligonucleotide TAG1, having the sequence SEQ ID NO: 25, and the oligonucleotide TAG2, having the sequence SEQ ID NO: 26. These two sequences are described in the sequence listing hereinafter. These two oligonucleotides make it possible to introduce the unique EcoRI and PstI sites into the coffee sequence amplified by PCR. They also make it possible to amplify the coffee DNA sequence encoding the coffee storage protein but lacking its cellular addressing sequence, called "signal peptide", which is between amino acids 1 and 26 of the sequence SEQ ID NO: 2. This strategy was followed so as to limit the toxic effects due to an overexpression in Escherichia coli of the proteins which contain very hydrophobic sequences.

This reaction is carried out in the presence of 50 ng of vector pCSP2, in a final volume of 100 μl containing 1.5 units of Pwo DNA polymerase (Boehringer Mannheim), 10 μl of 10× Pwo DNA polymerase buffer (Boehringer Mannheim), 0.1 mM of each DNTP and 2 nM of each olignucleotide, TAG1 and TAG2. The reaction mixture is incubated for 30 cycles (94° C.-30 s, 40° C.-60 s, 72° C.-2 min) followed by a final extension cycle at 72° C. for 7 min. 30 μl of the PCR mixture are then digested with the restriction enzymes EcoRI and PstI according to the recommendations provided by Promega (USA).

The coffee DNA fragment (1400 bp) amplified by PCR is separated by electrophoresis on a 0.8% agarose gel and it is purified according to the recommendations provided in the QIAquick Gel Extraction kit, (Qiagen Inc., 9600 De Soto Avenue, Chatsworth, Calif. 91311, USA). It is then ligated into the expression vector pQE31 (Qiagen, USA) previously digested with the enzymes. EcoRI and PstI and dephosphorylated by a calf intestinal alkaline phosphatase treatment. The use of the expression vector pQE31 makes it possible to introduce 6 histidines (6 His tag) in phase with the N-terminal end of the coffee 11s storage protein, which then facilitates the purification of this recombinant protein after passing over a column of Ni-NTA resin containing $Ni^{2+}$ ions (Hochuli et al., J. Chromatography, 411, 177–184, 1987).

The ligation mixture is used to transform competent cells of the strain M15 [pREP4] of Escherichia coli according to the recommendations provided by Qiagen (USA) and the recombinant bacteria are selected on dishes with LB medium containing 25 μg/ml of kanamycin and 100 μg/ml of ampicillin.

To test the expression of the coffee 11s storage protein in Escherichia coli, the bacteria are then cultured in 50 ml of liquid LB medium supplemented with the antibiotics as indicated above until an OD at 600 nm=1 is obtained. The induction is carried out by adding IPTG to a final concentration of 1 mM into the culture medium and culture samples are collected every 30 minutes. The bacteria are lysed and the soluble proteins are extracted from Escherichia coli under denaturing conditions. These proteins are then separated on a column of Ni-NTA resin following the protocol defined by QIAGEN (QIAexpress system). The protein fractions successively eluted are then analysed by SDS-PAGE electrophoresis. It is thus shown that the only protein capable of binding to the Ni-NTA column corresponds to the coffee 11s recombinant protein. This protein is expressed in Escherichia coli with an approximate molecular weight of 55 kDa which is in agreement with that observed in coffee beans for the storage protein in its precursor form, and this taking into consideration the protein sequence modifications which were carried out during the construction of the expression vector.

What is claimed is:

1. A recombinant storage protein comprising the amino acid sequence SEQ. ID NO:2.

2. A recombinant storage protein that comprises a sequence at least 95% homologous to SEQ ID NO:2.

3. An isolated storage protein comprising the amino acid sequence SEQ. ID NO:2.

4. A isolated storage protein that comprises a sequence at least 95% homologous to SEQ ID NO:2.

* * * * *

UNITED STATES PATENT AND TRADEMARK OFFICE
CERTIFICATE OF CORRECTION

PATENT NO. : 6,617,433 B1
DATED : September 9, 2003
INVENTOR(S) : Marraccini et al.

It is certified that error appears in the above-identified patent and that said Letters Patent is hereby corrected as shown below:

Title page,
Item [86], change the § 371(c)(1), (2), (4) Date from "April 11, 2000" to -- April 12, 2000 --.
Item [56], References Cited, insert the following,
-- FOREIGN PATENT DOCUMENTS
   EP   0 295 959      12/1988
   WO   91/19801      12/1991
   WO   92/17580      10/1992 --
OTHER PUBLICATIONS, please insert the following:

-- Database IntelliGenetics, FastDB- Fast Pairwise Comparison of Sequences, Accession NO: U64443, 25 January 1997.* --.
   -- Rogers et al., "An 11S-Type Storage Protein From *Coffee Arabica* L. Endosperm: Biochemical Characterization, Promoter Function and Expression During Grain Maturation", ASIC, 17th International Scientific Colloquium on Coffee, Nairobi, Kenya, pp. 161-168 (1997). --.
   -- Yuffa, et al., "Comparative Study of Protein Electrophoretic Patterns During Embryogenesis in *Coffea Arabica* cv Catimor," Plant Cell Reports, Vol. 13, pp. 197-202 (1994). --.
   -- Acuna, R., et al., "11S Storage Globulins from Coffee," EMBL database, XP002049318, January 25, 1997. --.
   -- Acuna, R., et al., "ACP93079," EMBL database, XP002084347, May 1, 1997. --.

Signed and Sealed this

Sixteenth Day of November, 2004

JON W. DUDAS
*Director of the United States Patent and Trademark Office*

SEQUENCE LISTING

```
<160> NUMBER OF SEQ ID NOS:  26

<210> SEQ ID NO 1
<211> LENGTH: 1706
<212> TYPE: DNA
<213> ORGANISM: Plant
<220> FEATURE:
<221> NAME/KEY: CDS
<222> LOCATION: (33)...(1508)

<400> SEQUENCE: 1
aaacacacta cactctcctc tgttgtcaga ga atg gct cac tct cat atg att         53
                                    Met Ala His Ser His Met Ile
                                     1               5 tct ctt tcc ttg tac gtt ctt ttg ttc ctc ggc tgt ttg gct caa cta        101
Ser Leu Ser Leu Tyr Val Leu Leu Phe Leu Gly Cys Leu Ala Gln Leu
             10                  15                  20 ggg aga cca cag cca agg ctc agg ggt aaa act cag tgc gat att cag        149
Gly Arg Pro Gln Pro Arg Leu Arg Gly Lys Thr Gln Cys Asp Ile Gln
     25                  30                  35 aag ctt aat gca caa gaa cca tcc ttc agg ttc cca tca gag gct ggt        197
Lys Leu Asn Ala Gln Glu Pro Ser Phe Arg Phe Pro Ser Glu Ala Gly
 40                  45                  50                  55 tta act gaa ttc tgg gat tct aat aat cca gaa ttt ggg tgc gct ggt        245
Leu Thr Glu Phe Trp Asp Ser Asn Asn Pro Glu Phe Gly Cys Ala Gly
             60                  65                  70
```

-continued

| | |
|---|---|
| gtg gaa ttt gag cgt aac act gtc caa cct aag ggc ctt cgt ttg cct<br>Val Glu Phe Glu Arg Asn Thr Val Gln Pro Lys Gly Leu Arg Leu Pro<br>        75                     80                       85 | 293 |
| cat tac tct aac gtg cct aaa ttc gtc tac gtt gtc gaa ggt acc ggt<br>His Tyr Ser Asn Val Pro Lys Phe Val Tyr Val Val Glu Gly Thr Gly<br>        90                     95                     100 | 341 |
| gtt caa ggc act gtg atc cct ggt tgt gct gaa aca ttt gaa tcc cag<br>Val Gln Gly Thr Val Ile Pro Gly Cys Ala Glu Thr Phe Glu Ser Gln<br>105                     110                     115 | 389 |
| ggt gaa tca ttt tgg ggt ggt cag gaa cag ccg ggc aaa ggg caa gaa<br>Gly Glu Ser Phe Trp Gly Gly Gln Glu Gln Pro Gly Lys Gly Gln Glu<br>120                     125                     130                     135 | 437 |
| ggc caa gag caa ggt tcc aaa ggt ggt cag gaa ggg cga agg caa agg<br>Gly Gln Glu Gln Gly Ser Lys Gly Gly Gln Glu Gly Arg Arg Gln Arg<br>                 140                     145                     150 | 485 |
| ttt cca gac cgc cat cag aag ctc aga agg ttc caa aaa gga gat gtc<br>Phe Pro Asp Arg His Gln Lys Leu Arg Arg Phe Gln Lys Gly Asp Val<br>                 155                     160                     165 | 533 |
| ctt ata ttg ctt cct ggt ttc act cag tgg aca tat aat gat gga gat<br>Leu Ile Leu Leu Pro Gly Phe Thr Gln Trp Thr Tyr Asn Asp Gly Asp<br>170                     175                     180 | 581 |
| gtt cca ctt gtc act gtc gca ctt ctt gat gtt gcc aat gag gct aat<br>Val Pro Leu Val Thr Val Ala Leu Leu Asp Val Ala Asn Glu Ala Asn<br>185                     190                     195 | 629 |
| cag ctt gat ttg cag tcc aag aaa ttt ttc cta gcc gga aac ccg caa<br>Gln Leu Asp Leu Gln Ser Lys Lys Phe Phe Leu Ala Gly Asn Pro Gln<br>200                     205                     210                     215 | 677 |
| cag ggt ggt gga aag gaa ggc cat caa ggc cag cag cag cag cat aga<br>Gln Gly Gly Gly Lys Glu Gly His Gln Gly Gln Gln Gln Gln His Arg<br>                 220                     225                     230 | 725 |
| aac atc ttc tca gga ttt gat gac caa ctt ttg gct gat gct ttc aat<br>Asn Ile Phe Ser Gly Phe Asp Asp Gln Leu Leu Ala Asp Ala Phe Asn<br>                 235                     240                     245 | 773 |
| gtt gac ctc aaa ata ata cag aaa ttg aag ggt ccg aaa gat caa agg<br>Val Asp Leu Lys Ile Ile Gln Lys Leu Lys Gly Pro Lys Asp Gln Arg<br>250                     255                     260 | 821 |
| ggt agc aca gtc cga gct gaa aaa ctt caa ctg ttc ctg cct gaa tat<br>Gly Ser Thr Val Arg Ala Glu Lys Leu Gln Leu Phe Leu Pro Glu Tyr<br>265                     270                     275 | 869 |
| agt gag caa gtg caa caa ccc caa caa cag cag gag cag caa caa cat<br>Ser Glu Gln Val Gln Gln Pro Gln Gln Gln Gln Glu Gln Gln Gln His<br>280                     285                     290                     295 | 917 |
| ggt gtt gga aga gga tgg aga tcc aac gga ctt gag gaa act ttg tgc<br>Gly Val Gly Arg Gly Trp Arg Ser Asn Gly Leu Glu Glu Thr Leu Cys<br>                 300                     305                     310 | 965 |
| acg gtg aag ctt agt gaa aac att ggc ctc ccc caa gag gct gat gta<br>Thr Val Lys Leu Ser Glu Asn Ile Gly Leu Pro Gln Glu Ala Asp Val<br>                 315                     320                     325 | 1013 |
| ttc aat cct cgt gct ggc cgc att acc act gtt aat agc caa aag att<br>Phe Asn Pro Arg Ala Gly Arg Ile Thr Thr Val Asn Ser Gln Lys Ile<br>                 330                     335                     340 | 1061 |
| cct atc ctc agc agc ctc caa ctt agt gca gaa aga gga ttc ctc tac<br>Pro Ile Leu Ser Ser Leu Gln Leu Ser Ala Glu Arg Gly Phe Leu Tyr<br>345                     350                     355 | 1109 |
| agc aat gcc att ttt gca cca cac tgg aat atc aat gca cat aat gcc<br>Ser Asn Ala Ile Phe Ala Pro His Trp Asn Ile Asn Ala His Asn Ala<br>360                     365                     370                     375 | 1157 |
| ctg tat gtg att aga gga aat gca aga att cag gtg gtg gat cac aaa<br>Leu Tyr Val Ile Arg Gly Asn Ala Arg Ile Gln Val Val Asp His Lys<br>                 380                     385                     390 | 1205 |

-continued

```
gga aac aaa gtt ttt gac gat gaa gta aaa cag ggt cag cta ata att      1253
Gly Asn Lys Val Phe Asp Asp Glu Val Lys Gln Gly Gln Leu Ile Ile
            395                 400                 405 gtg cca caa tac ttt gct gtg atc aag aaa gct gga aac caa gga ttt      1301
Val Pro Gln Tyr Phe Ala Val Ile Lys Lys Ala Gly Asn Gln Gly Phe
            410                 415                 420 gag tac gtt gca ttc aag acg aac gac aat gcc atg att aac cca ctt      1349
Glu Tyr Val Ala Phe Lys Thr Asn Asp Asn Ala Met Ile Asn Pro Leu
        425                 430                 435 gtt gga aga ctt tcg gca ttt cga gca att cct gag gaa gtt ttg agg      1397
Val Gly Arg Leu Ser Ala Phe Arg Ala Ile Pro Glu Glu Val Leu Arg
440                 445                 450                 455 agc tct ttc caa att tcc agc gag gaa gct gag gaa ttg aag tat gga      1445
Ser Ser Phe Gln Ile Ser Ser Glu Glu Ala Glu Glu Leu Lys Tyr Gly
                460                 465                 470 aga cag gag cgt ttg ctt ttg agt gag cag tct cag cag ggg aaa aag      1493
Arg Gln Glu Arg Leu Leu Leu Ser Glu Gln Ser Gln Gln Gly Lys Lys
            475                 480                 485 aga agt tgc ttg agc taattatgta aaataatcg tatattagtc catgcatagt       1548
Arg Ser Cys Leu Ser
            490 ctaccaacta tatgtgtgaa tctaattcca aaataaaatg gtcaatggat gtaaagacat    1608 ggcaatccaa gccttactac tggcgttgat tgcgagaagt ttgatgtttg gtgaccatga    1668 gtcaataata aactatgata attaatgtaa aattttcc                            1706

<210> SEQ ID NO 2
<211> LENGTH: 492
<212> TYPE: PRT
<213> ORGANISM: Plant

<400> SEQUENCE: 2

Met Ala His Ser His Met Ile Ser Leu Ser Leu Tyr Val Leu Leu Phe
 1               5                  10                  15

Leu Gly Cys Leu Ala Gln Leu Gly Arg Pro Gln Pro Arg Leu Arg Gly
            20                  25                  30

Lys Thr Gln Cys Asp Ile Gln Lys Leu Asn Ala Gln Glu Pro Ser Phe
         35                  40                  45

Arg Phe Pro Ser Glu Ala Gly Leu Thr Glu Phe Trp Asp Ser Asn Asn
     50                  55                  60

Pro Glu Phe Gly Cys Ala Gly Val Glu Phe Glu Arg Asn Thr Val Gln
 65                  70                  75                  80

Pro Lys Gly Leu Arg Leu Pro His Tyr Ser Asn Val Pro Lys Phe Val
                 85                  90                  95

Tyr Val Glu Gly Thr Gly Val Gln Gly Thr Val Ile Pro Gly Cys
                100                 105                 110

Ala Glu Thr Phe Glu Ser Gln Gly Glu Ser Phe Trp Gly Gly Gln Glu
            115                 120                 125

Gln Pro Gly Lys Gly Gln Glu Gln Glu Gln Gly Ser Lys Gly Gly
        130                 135                 140

Gln Glu Gly Arg Arg Gln Arg Phe Pro Asp Arg His Gln Lys Leu Arg
145                 150                 155                 160

Arg Phe Gln Lys Gly Asp Val Leu Ile Leu Leu Pro Gly Phe Thr Gln
                165                 170                 175

Trp Thr Tyr Asn Asp Gly Asp Val Pro Leu Val Thr Val Ala Leu Leu
            180                 185                 190
```

-continued

```
Asp Val Ala Asn Glu Ala Asn Gln Leu Asp Leu Gln Ser Lys Lys Phe
            195                 200                 205

Phe Leu Ala Gly Asn Pro Gln Gln Gly Gly Lys Glu Gly His Gln
        210                 215                 220

Gly Gln Gln Gln Gln His Arg Asn Ile Phe Ser Gly Phe Asp Asp Gln
225                 230                 235                 240

Leu Leu Ala Asp Ala Phe Asn Val Asp Leu Lys Ile Ile Gln Lys Leu
                245                 250                 255

Lys Gly Pro Lys Asp Gln Arg Gly Ser Thr Val Arg Ala Glu Lys Leu
            260                 265                 270

Gln Leu Phe Leu Pro Glu Tyr Ser Glu Gln Val Gln Gln Pro Gln Gln
        275                 280                 285

Gln Gln Glu Gln Gln Gln His Gly Val Gly Arg Gly Trp Arg Ser Asn
290                 295                 300

Gly Leu Glu Glu Thr Leu Cys Thr Val Lys Leu Ser Glu Asn Ile Gly
305                 310                 315                 320

Leu Pro Gln Glu Ala Asp Val Phe Asn Pro Arg Ala Gly Arg Ile Thr
                325                 330                 335

Thr Val Asn Ser Gln Lys Ile Pro Ile Leu Ser Ser Leu Gln Leu Ser
            340                 345                 350

Ala Glu Arg Gly Phe Leu Tyr Ser Asn Ala Ile Phe Ala Pro His Trp
        355                 360                 365

Asn Ile Asn Ala His Asn Ala Leu Tyr Val Ile Arg Gly Asn Ala Arg
370                 375                 380

Ile Gln Val Val Asp His Lys Gly Asn Lys Val Phe Asp Asp Glu Val
385                 390                 395                 400

Lys Gln Gly Gln Leu Ile Ile Val Pro Gln Tyr Phe Ala Val Ile Lys
                405                 410                 415

Lys Ala Gly Asn Gln Gly Phe Glu Tyr Val Ala Phe Lys Thr Asn Asp
            420                 425                 430

Asn Ala Met Ile Asn Pro Leu Val Gly Arg Leu Ser Ala Phe Arg Ala
        435                 440                 445

Ile Pro Glu Glu Val Leu Arg Ser Ser Phe Gln Ile Ser Ser Glu Glu
        450                 455                 460

Ala Glu Glu Leu Lys Tyr Gly Arg Gln Glu Arg Leu Leu Leu Ser Glu
465                 470                 475                 480

Gln Ser Gln Gln Gly Lys Lys Arg Ser Cys Leu Ser
                485                 490
```

<210> SEQ ID NO 3
<211> LENGTH: 3477
<212> TYPE: DNA
<213> ORGANISM: Plant

<400> SEQUENCE: 3

```
tttaaaagtt tggtagaaaa tttgagatat tgacgtctca cgaggccaga tatcaatttg      60
ctgttggtgt gattaacaag tttatgaaaa atccacgtca gtcacatttg taggcggtta     120
agaagatttt gaaatatatt gaaagtactc acagtgttgg catttttat  tcagaaaatt     180
atccagttga atggtttggc tactgatagt tattgagcag gtgatacaat agaagaagaag   240
agtacttcaa gttatgcatt ttttattggt tctgacgtat tttcctcgag ttcaaagaaa     300
caacaggtga ttgcattgtt tacagcagaa gcagagtata ttgcagcggc taatagtgct     360
aatcaagttt tgtggttacg ttgcatgttt ggtattctac aatacaagca ggttgatctt    420
```

```
acgaaaattt attgtgatag taagtcagct attgaattgt ccaagaattt agtacttcat    480
ggatgtaaca agcatattgg catcaaatat cacttcacac gtgagttggt tcgagagaga    540
gagagaggtt gaaattgatt attgcagaat taaatagtaa gtggctgaca ttttcaccaa    600
gacattgaag atagagattt ttgtcaagtt gaagaatatg ttaggcatgt ccaagttaga    660
ggagattcgt taatggagg caatatagaa acacaaacca agcctttatt atttgtttat    720
gctgtcatgt gggattggta gtagtattgt tggttggtag ggtggtcaca tgggattgaa    780
tttcctatga ctagtagagt tagtaataga agttagccgc aaggggtttt tgatgtgtag    840
ctgttgcgtc cgtctttttt agccttaaga agaagtagtc acctccgttg tgttctgcat    900
ggtgtagcag agccttgtta tgattaatag aaaattttcc tttgcctcaa tatcgttttt    960
tttttttatt gtttctgtgg gttttgtgta tttatcaatt tgggtccacc actttttcca    1020
accatgatct taagcatatc agctcacttc cactctattt ctttaccatg attttaagta    1080
caataatttc ctaaaaaacc aaaaagaat catatctata aattttgaga aaagcatata    1140
tactgctaac atgattctac gtataatagt ggattattaa aaattattaa ttacatattt    1200
ttgacataac catcggtgta ccaaaagcac taatgattac aacactaaac acgcaaagtt    1260
gagtaattga aactgaaatt acacatagac aaaaactcaa ctaaacaatg ttagaatgga    1320
atagattaga gaaccattga atgatctaac tctggaactg gggttaagac agtcttccca    1380
agcaactttt tttgtccatg atttggctat catatcacta tcttgaaatt tgttcagaca    1440
cactgtggga ggctggaatc aatagcttgg acttggatca tttatagaag ctgatgatca    1500
ttattgctca acatatgaat ttgatacaaa tgtcagtgga atcaacttcg tactttttt    1560
ttttcctctt ttctttttgga gtacaagcct acctacaagg ggaaggatag aggaaatgca    1620
tagagggaga tttaacctct acccaagcgg cagatacaat gggtcacgat acagctggtt    1680
tattgatgta ttacagcgga aaacgatgta gatgagcaac cttttcaaag aacataagtc    1740
aaaatcatag atgtaaagca gtcaactgag tctgtggcaa ttgttagacg taaaactcta    1800
ttccatgtca ttattaggtt tcttgctcta tcttttagtt tgatccaaca tggattggct    1860
gtcttttgtt tgctaataaa gattttaaat catggaattt ccctgtagaa tgcctttaat    1920
tacatgccac tagactagaa acggtaattg tttaacagat attattcca ggcattgaaa    1980
ttatgaactg caacagtcat ttgcctagaa gtgtaaacca attgtcttca ataaaggtga    2040
ataaaaatcg atgaagatag ataggtgcta gaaacttaaa agcagaagat gataggtgtg    2100
atgtaatacg cagcagtagt gatcatcttt ccatatcaca tcttgaaaga tcccaagatg    2160
aatgtgtgtt tgatttgggg tttgattcat caaaagccat cgtagcagat aatgcacctt    2220
accatgccat tgctaaagta caaaaatttc atgcaaatac aaacacaaaa gattgaacaa    2280
tacatgtcag aaactctatg ccaccaaggc ttacacatca tctttggtgt aaagaagtgt    2340
tcatcttcat cagccatgca caagactgag tagccaagtg taaaatgaaa attttgacgt    2400
gtcgattcct catcttccat tacatgttat aaaaggagcc atttccaagc tctaatcgcc    2460
gcatcccctc accacaaaaa cacatcacac tctcctctgt tgtcagagaa tggctcactc    2520
tcatatgatt tctcttttcct tgtacgttct tttgttcctc ggctgtttgg ctcaactagg    2580
gagaccacag ccaaggctca ggggtaaaac tcagtgcgat attcagaagc ttaatgcaca    2640
agaaccatcc ttcaggttcc catcagaggc tggtttaact gaattctggg attctaataa    2700
tccagaattt gggtgcgctg gtgtggaatt tgagcgtaac actgtccaac ctaagggcct    2760
tcgtttgcct cattactcta acgtgcctaa attcgtctac gttgtcgaag gcagtttcat    2820
```

-continued

```
ttcccatcct ttccattatt tctggagttt tttttctatt ttcttcttaa tcatcgtatt    2880
attcattttc ttcatgattt aatcattttg gcataatgca ggtaccggtg ttcaaggcac    2940
tgtgatccct ggttgtgctg aaacatttga atcccagggt gaatcatttt ggggtggtca    3000
ggaacagccg ggcaaagggc aagaaggcca agagcaaggt tccaaaggtg gtcaggaagg    3060
gcgaaggcaa aggtttccag accgccatca gaagctcaga aggttccaaa aaggagatgt    3120
ccttatattg cttcctggtt tcactcagtg gacatataat gatggagatg ttccacttgt    3180
cactgtcaca cttcttgatg ttgccaatga cgtgaatcag cttgatttgc agtccagggt    3240
aagaaaactt tcaatccaaa cttgccaagt attaatcaaa aaataatctc tttctgggca    3300
tattttattg cggtaccact ttaataaaaa aaaaatttta tactttcaga aatttttcct    3360
agccggaaac ccgcaacagg gtggtggaaa ggaaggccat caaggccagc agcagcagca    3420
tagaaacatc ttctcaggat ttgatgacca cttttggctg atgctttcaa tgttgac      3477
```

```
<210> SEQ ID NO 4
<211> LENGTH: 17
<212> TYPE: DNA
<213> ORGANISM: Plant
<220> FEATURE:
<221> NAME/KEY: misc_feature
<222> LOCATION: (1)...(17)
<223> OTHER INFORMATION: n = A,T,C or G

<400> SEQUENCE: 4
gcngaygtnt tyaaycc                                                     17

<210> SEQ ID NO 5
<211> LENGTH: 17
<212> TYPE: DNA
<213> ORGANISM: Plant

<400> SEQUENCE: 5
aaacattggc ctcccc                                                      17

<210> SEQ ID NO 6
<211> LENGTH: 19
<212> TYPE: DNA
<213> ORGANISM: Plant

<400> SEQUENCE: 6
ccaaacatca aacttctcg                                                   19

<210> SEQ ID NO 7
<211> LENGTH: 23
<212> TYPE: DNA
<213> ORGANISM: Plant

<400> SEQUENCE: 7
gagaaatcat atgagagtga gcc                                              23

<210> SEQ ID NO 8
<211> LENGTH: 23
<212> TYPE: DNA
<213> ORGANISM: Plant

<400> SEQUENCE: 8
ttcttttgtt cctcggctgt ttg                                              23

<210> SEQ ID NO 9
```

-continued

```
<211> LENGTH: 17
<212> TYPE: DNA
<213> ORGANISM: Plant

<400> SEQUENCE: 9
gtgagccatt ctctgac                                                        17

<210> SEQ ID NO 10
<211> LENGTH: 23
<212> TYPE: DNA
<213> ORGANISM: Plant

<400> SEQUENCE: 10
agtttgatcc aacatggatt ggc                                                 23

<210> SEQ ID NO 11
<211> LENGTH: 24
<212> TYPE: DNA
<213> ORGANISM: Plant

<400> SEQUENCE: 11
gcaagaaacc taataatgac atgg                                                24

<210> SEQ ID NO 12
<211> LENGTH: 20
<212> TYPE: DNA
<213> ORGANISM: Plant

<400> SEQUENCE: 12
cctcttttct tttggagtac                                                     20

<210> SEQ ID NO 13
<211> LENGTH: 12
<212> TYPE: DNA
<213> ORGANISM: Plant

<400> SEQUENCE: 13
cgcggatccg cg                                                             12

<210> SEQ ID NO 14
<211> LENGTH: 33
<212> TYPE: DNA
<213> ORGANISM: Plant

<400> SEQUENCE: 14
cgcggatccg cgatgagagt gagccattct ctg                                      33

<210> SEQ ID NO 15
<211> LENGTH: 35
<212> TYPE: DNA
<213> ORGANISM: Plant

<400> SEQUENCE: 15
cgcggatccg cgcctctttt cttttggagt acaag                                    35

<210> SEQ ID NO 16
<211> LENGTH: 36
<212> TYPE: DNA
<213> ORGANISM: Plant

<400> SEQUENCE: 16
cgcggatccg cgtaggtttc ttgctctatc ttttag                                   36
```

```
<210> SEQ ID NO 17
<211> LENGTH: 36
<212> TYPE: DNA
<213> ORGANISM: Plant

<400> SEQUENCE: 17
cgcggatccg cggtgctaga aacttaaaag cagaag                               36

<210> SEQ ID NO 18
<211> LENGTH: 36
<212> TYPE: DNA
<213> ORGANISM: Plant

<400> SEQUENCE: 18
cgcggatccg cgacaaaaga ttgaacaata catgtc                               36

<210> SEQ ID NO 19
<211> LENGTH: 30
<212> TYPE: DNA
<213> ORGANISM: Plant

<400> SEQUENCE: 19
tttgatttca cgggttgggg tttctacagg                                      30

<210> SEQ ID NO 20
<211> LENGTH: 30
<212> TYPE: DNA
<213> ORGANISM: Plant

<400> SEQUENCE: 20
ggctcgtatg ttgtgtggaa ttgtgagcgg                                      30

<210> SEQ ID NO 21
<211> LENGTH: 18
<212> TYPE: DNA
<213> ORGANISM: Plant

<400> SEQUENCE: 21
atgttacgtc ctgtagaa                                                   18

<210> SEQ ID NO 22
<211> LENGTH: 18
<212> TYPE: DNA
<213> ORGANISM: Plant

<400> SEQUENCE: 22
gcaaagtccc gctagtgc                                                   18

<210> SEQ ID NO 23
<211> LENGTH: 17
<212> TYPE: DNA
<213> ORGANISM: Plant

<400> SEQUENCE: 23
ctggatcgtt tcgcatg                                                    17

<210> SEQ ID NO 24
<211> LENGTH: 16
<212> TYPE: DNA
<213> ORGANISM: Plant

<400> SEQUENCE: 24
ccagagtccc gctcag                                                     16
```

```
<210> SEQ ID NO 25
<211> LENGTH: 30
<212> TYPE: DNA
<213> ORGANISM: Plant

<400> SEQUENCE: 25
actaggggat ccacagccaa ggctcagggg                              30

<210> SEQ ID NO 26
<211> LENGTH: 36
<212> TYPE: DNA
<213> ORGANISM: Plant

<400> SEQUENCE: 26
gtactctgca gacataatta gctcaagcaa cttccc                       36
```